United States Patent [19]

Nguyen

[11] Patent Number: 5,329,041

[45] Date of Patent: Jul. 12, 1994

[54] TRISUBSTITUTED BENZOIC ACID INTERMEDIATES

[75] Inventor: Nhan H. Nguyen, Hercules, Calif.

[73] Assignee: Imperial Chemical Industries PLC, London, England

[21] Appl. No.: 75,006

[22] Filed: Jun. 10, 1993

Related U.S. Application Data

[60] Continuation of Ser. No. 809,567, Dec. 17, 1991, abandoned, which is a division of Ser. No. 641,206, Jan. 15, 1991, Pat. No. 5,110,979.

[51] Int. Cl.$^5$ .................................. C07C 205/00
[52] U.S. Cl. ................................................ 560/23
[58] Field of Search ............................ 560/23; 562/434

[56] References Cited

U.S. PATENT DOCUMENTS

| | | | |
|---|---|---|---|
| 2,691,025 | 10/1954 | Clinton et al. | 562/434 |
| 3,013,053 | 12/1961 | Richter et al. | 560/23 |
| 3,211,611 | 10/1965 | Clark et al. | 560/23 |
| 3,439,019 | 4/1969 | Sarett et al. | 560/23 |
| 4,016,193 | 4/1977 | Kobayashi et al. | 560/23 |
| 4,762,551 | 8/1988 | Knudsen | 560/23 |
| 4,767,447 | 8/1988 | Lee et al. | 560/23 |
| 4,808,338 | 2/1989 | Lee | 560/23 |
| 4,816,066 | 3/1989 | Michaely et al. | 71/123 |
| 4,822,906 | 4/1989 | Carter | 558/416 |
| 4,918,236 | 4/1990 | Knudsen et al. | 560/23 |
| 5,026,896 | 6/1991 | Michaely et al. | 560/23 |
| 5,092,919 | 3/1992 | Nguyen | 560/23 |

FOREIGN PATENT DOCUMENTS

| | | | |
|---|---|---|---|
| 751979 | 12/1970 | Fed. Rep. of Germany | 560/23 |
| 2-454448 | 2/1990 | Japan | 560/23 |

OTHER PUBLICATIONS

Chemical Abstracts, vol. 110, No. 11, Entry 95226e (1988).
Feiser et al., "Reagents for Organic Synthesis", pp. 767–772 (1967).

*Primary Examiner*—José G. Dees
*Assistant Examiner*—Keith MacMillan
*Attorney, Agent, or Firm*—William E. Dickheiser

[57] ABSTRACT

2-methyl-3-(substituted)-4-(substituted) benzoic acids or their alkyl ester that are useful to prepare herbicidal compounds.

2 Claims, No Drawings

TRISUBSTITUTED BENZOIC ACID INTERMEDIATES

This is a continuation of copending application Ser. No. 07/809,567 filed on Dec. 17, 1991, now abandoned which is a divisional application of U.S. application Ser. No. 07/641,206, filed Jan. 15, 1991, now U.S. Pat. No. 5,110,979, issued May 5, 1992.

BACKGROUND OF THE INVENTION

Certain 2-(2'3'4'trisubstituted benzoyl)-1,3-cyclohexanedione herbicides are described in U.S. Pat. No. 4,816,066, issued Mar. 28, 1989 and a U.S. application entitled 2-(2'methyl,3'4'-trisubstituted benzoyl)-1,3-cyclohexanediones, with Nhan H. Nguyen, inventor, filed herewith, and both incorporated herein by reference.

The above-described herbicidal compounds can have the following structural formula

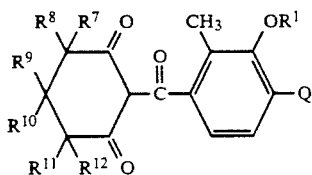

wherein $R^7$ through $R^{12}$ are hydrogen or $C_1$-$C_4$ alkyl; $R^1$ is $C_1$-$C_4$ alkyl or $C_1$-$C_4$ haloalkyl, —$CH_2CH_2OCH_3$, —$CH_2CH_2OC_2H_5$, Q is halogen (chlorine, bromine, iodine, or fluorine), nitro, or $S(O)_nR^2$ wherein $R^2$ is $C_1$-$C_4$ alkyl; and n is the integer 0 or 2.

These herbicides can be prepared by reacting a dione of the structural formula

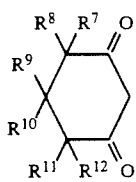

wherein $R^7$ through $R^{12}$ are as defined with a mole of trisubstituted benzoyl chloride of the structural formula

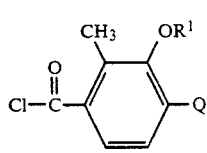

wherein $R^1$ and Q are as defined above.

DESCRIPTION OF THE INVENTION

This invention has several embodiments which are as follows:

Embodiment A relates to novel intermediate compounds having the structural formula

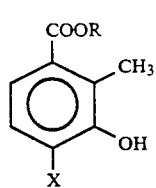

wherein R is $C_1$-$C_4$ alkyl, preferably ethyl and X is halogen, preferably chlorine and bromine.

The term "halogen" as used herein means chlorine, bromine, iodine or fluorine.

Embodiment B relates to novel intermediate compounds having the structural formula

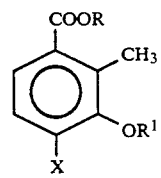

wherein X is halogen preferably chlorine and bromine; R is $C_1$-$C_4$ alkyl, preferably ethyl; and $R^1$ is $C_1$-$C_4$ alkyl, preferably $C_1$-$C_2$ alkyl; $C_1$-$C_4$ haloalkyl, preferably trifluoromethyl; —$CH_2CH_2OCH_3$ or —$CH_2CH_2OC_2H_5$.

Embodiment C relates to novel intermediate compounds having the structural formula

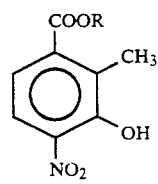

wherein R is $C_1$-$C_4$ alkyl, preferably ethyl.

Embodiment D relates to novel intermediate compounds having the structural formula

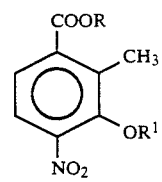

wherein R is $C_1$-$C_4$ alkyl, preferably ethyl; $R^1$ is $C_1$-$C_4$ alkyl, preferably $C_1$-$C_2$ alkyl or $C_1$-$C_4$ haloalkyl; —$CH_2CH_2OCH_3$ or —$CH_2CH_2OC_2H_5$.

Embodiment E relates to novel intermediate compounds having the structural formula

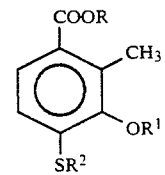

wherein R is $C_1$-$C_4$ alkyl, preferably ethyl; $R^1$ is $C_1$-$C_4$ alkyl, preferably $C_1$-$C_2$ alkyl or $C_1$-$C_4$ haloalkyl;

—CH₂CH₂OCH₃ or —CH₂CH₂OC₂H₅; and R² is C₁–C₄ alkyl; preferably methyl, ethyl or n-propyl.

Embodiment F relates to novel intermediate compounds having the structural formula

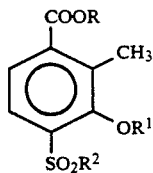

wherein R is C₁–C₄ alkyl, preferably ethyl; R¹ is C₁–C₄ alkyl, preferably C₁–C₂ alkyl; C₁–C₄ haloalkyl, preferably trifluoromethyl; —CH₂CH₂OCH₃ or —CH₂CH₂OC₂H₅; and R² is C₁–C₄ alkyl, preferably methyl, ethyl or n-propyl.

Embodiment G relates to novel intermediate compounds having the structural formula

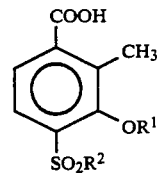

wherein R¹ is C₁–C₄ alkyl, preferably C₁–C₂ alkyl; C₁–C₄ haloalkyl, preferably trifluormethyl; —CH₂CH₂OCH₃ or —CH₂CH₂OC₂H₅; and R² is C₁–C₄ alkyl, preferably methyl, ethyl or n-propyl.

The several intermediate compounds of this invention can be prepared by the general method shown in the schematic drawing of the next page wherein X, R, R¹ and R² are as defined.

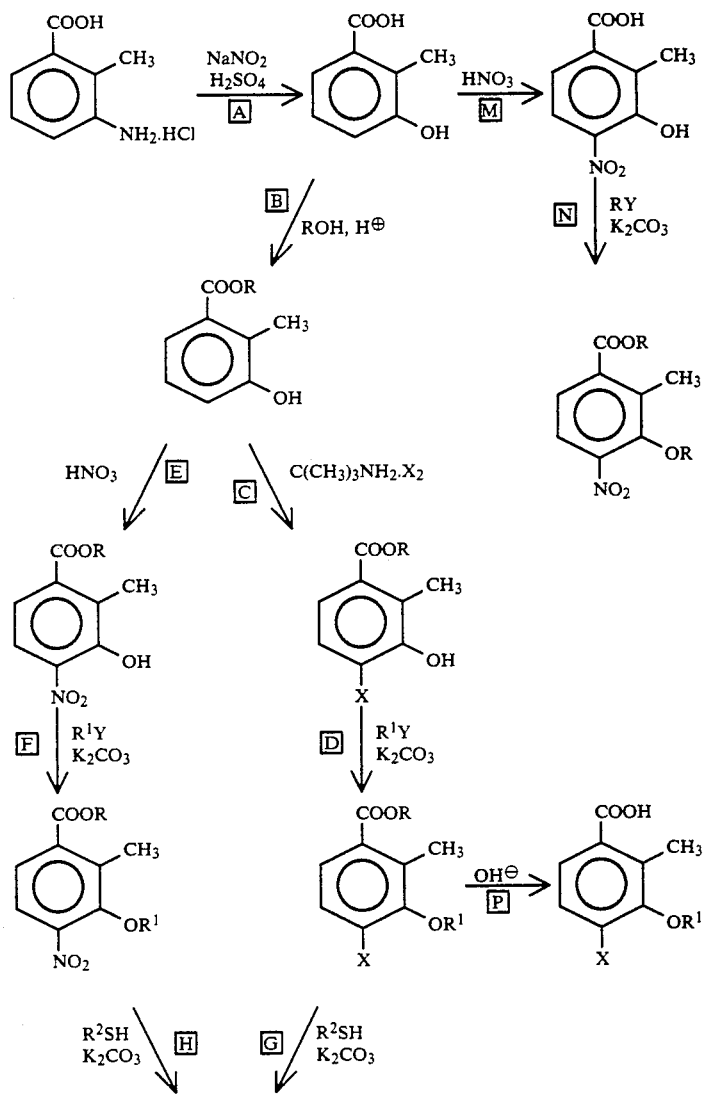

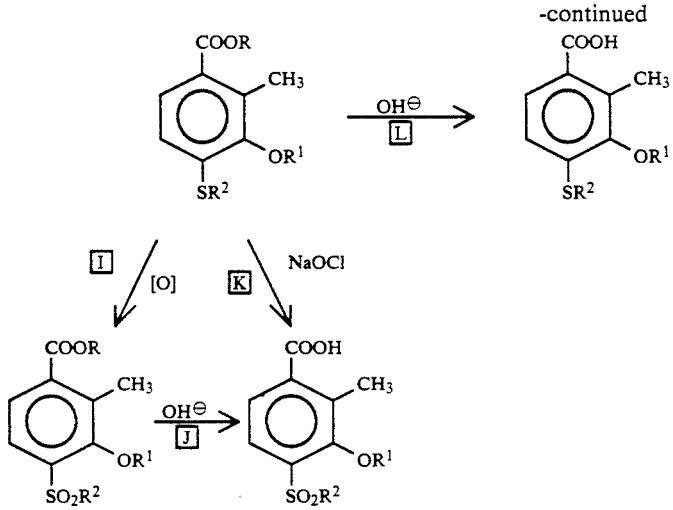

Referring to the schematic drawing, and particularly to Reaction Steps (A) through (J) consider the following:

Generally in Reaction Step (A), a mole amount of anilinium hydrochloride is reacted slowly with a slight mole excess of sodium nitrate and a mole excess of sulfuric acid. The reaction temperature is maintained at about 0° to 15° C. until a solution is obtained. The solution slowly is added to a heated aqueous solution of sulfuric acid and heated to reflux. A solid reaction product is recovered and purified by conventional techniques.

For Reaction Step (B), 2-methyl-3-hydroxy benzoic acid is reacted with a $C_1$-$C_4$ alcohol with concentrated sulfuric acid at reflux temperatures. The reaction product is recovered and purified by conventional techniques.

For Reaction Step (C), a mole amount of a $C_1$-$C_4$ alkyl ester of 2-methyl-3-hydroxy benzoic acid is reacted with a mole amount of a tertiary butyl amine and a mole of bromine or chlorine in a solvent such as methylene chloride at temperatures from $-50°$ C. to room temperature.

For Reaction Step (D), a mole amount of a $C_1$-$C_4$ alkyl ester of 2-methyl-3-hydroxy-4-bromobenzoic acid is alkylated with a mole amount of the requisite alkylating agent such as a $C_1$-$C_4$ alkyl iodide or chloride or a di-$C_1$-$C_4$ alkyl sulfate and a mole amount of a base such as potassium carbonate in a solvent such as a mixture of acetone and dimethyformamidine (DMF). The reaction can be run at reflux temperatures and the reaction product recovered by conventional techniques.

For Reaction Step (E), a mole amount of a $C_1$-$C_4$ alkyl ester of 2-methyl-3-hydroxy benzoic acid is reacted with at least two mole of nitric acid in glacial acetic acid. The reaction can be run at room temperature. The reaction product is recovered by conventional techniques.

For Reaction Step (F) is carried out by reacting a mole of a $C_1$-$C_4$ alkyl ester of 2-methyl-3-hydroxy-4-nitrobenzoic acid with a mole amount of the requisite alkylating agent such as $C_1$-$C_4$ alkyl chloride or iodide or a di-$C_1$-$C_4$ alkyl sulfate and a mole amount of a base such as potassium carbonate in a solvent such as a mixture of acetone and DMF. The reaction can be run at reflux temperatures and the reaction product recovered by conventional techniques.

For Reaction Step (G) is carried out by reacting a mole amount of a $C_1$-$C_4$ alkyl ester of 2-methyl-3-($C_1$-$C_4$ alkoxy, $C_1$-$C_4$ haloalkoxy, 2-methoxyethoxy or 2-ethoxyethoxy)-4-bromobenzoic acid with a mole amount of a $C_1$-$C_4$ alkyl mercaptan along with a mole excess of a base such as potassium carbonate in a solvent such as dimethylformamide. The reaction is run for several hours at a temperature between 50° C. to 100° C. with stirring under an inert atmosphere such as nitrogen. The desired reaction product recovered by conventional techniques.

Reaction Step (G) can also be rerun by reacting a mole amount of a $C_1$-$C_4$ alkyl ester of 2-methyl-3-($C_1$-$C_4$ alkoxy, $C_1$-$C_4$ haloalkoxy 2-methoxyethoxy or 2-ethoxyethoxy)-4-bromobenzoic acid with a mole amount of a $C_1$-$C_4$ alkylthioglycolate according to the teaching of U.S. application Ser. No. 07/590,115, filed Sep. 28, 1990 and entitled "Improved Method for the Preparation of 4-Methylsulfonyl Benzoic Acid Derivatives and Intermediates", incorporated herein by reference.

For Reaction Step (H) is run by reacting a mole amount of a $C_1$-$C_4$ alkyl ester of 2-methyl-3-($C_1$-$C_4$ alkoxy, $C_1$-$C_4$ haloalkoxy, 2-methoxyethoxy or 2-ethoxyethoxy)-4-nitrobenzoic acid with a mole amount of a $C_1$-$C_4$ alkyl mercaptan along with a mole excess of a base such as potassium carbonate in a solvent such as dimethylformamide. The reaction is run for several hours at a temperature between 50° C. to 100° C. with stirring under an inert atmosphere such as nitrogen. The desired reaction product recovered by conventional techniques.

Reaction Step (H) can also be rerun by reacting a mole amount of a $C_1$-$C_4$ alkyl ester of 2-methyl-3-($C_1$-$C_4$ alkoxy, $C_1$-$C_4$ haloalkoxy, 2-methoxyethoxy or 2-ethoxyethoxy)-4-nitrobenzoic acid with a mole amount of a $C_1$-$C_4$ alkylthioglycolate according to the teaching of U.S. application Ser. No. 07/590,115, filed Sep. 28, 1990 and entitled "Improved Method for the Preparation of 4-Methylsulfonyl Benzoic Acid Derivatives and Intermediates", incorporated herein by reference.

For Reaction Step (I) is carried out by reacting a mole amount of a $C_1$-$C_4$ alkyl ester of 2-methyl-3-($C_1$-$C_4$ alkoxy, $C_1$-$C_4$ haloalkoxy, 2-methoxyethoxy or 2-ethoxyethoxy)-4-($C_1$-$C_4$ alkylthio)benzoic acid with at least 3 mole of an oxidizing agent such as acetyl peroxyacid or m-chloroperbenzoic acid in a suitable solvent such as methylene chloride by stirring a solution of the reactants at 20° to 40° C. The desired reaction product is recovered by conventional techniques. During this reaction step the $C_1$–$C_4$ alkylthio substituent is oxidized to the corresponding $C_1$–$C_4$ alkylsulfonyl substituent without hydrolysis of the ester group to an acid group.

For Reaction Step (J), a $C_1$–$C_4$ alkyl ester of 2-methyl-3-($C_1$–$C_4$ alkoxy, $C_1$–$C_4$ haloalkoxy, 2-methoxyethoxy or 2-ethoxyethoxy)-4-($C_1$–$C_4$ alkylsulfonyl)benzoic acid is hydrolyzed to the corresponding trisubstituted benzoic acid by reaction with a mole amount of sodium hydroxide in an aqueous medium. The hydrolysis is run at a temperature of between 20° to 100° C. with stirring. The reaction product is recovered by conventional techniques.

For Reaction Step (K) is run by reacting a mole amount of a $C_1$–$C_4$ alkyl ester of 2-methyl-3-($C_1$–$C_4$ alkoxy, $C_1$–$C_4$ haloalkoxy 2-methoxyethoxy or 2-ethoxyethoxy)-4-($C_1$–$C_4$ alkylthio)benzoic acid with at least 5 mole of an oxidizing agent such as sodium hypochlorite in a suitable solvent such as dioxane by heating a solution of the reactants at a temperature of 60° to 80° C. After an exothermic reaction the mixture is cooled and acidified with hydrochloric acid. The desired trisubstituted benzoic acid intermediate is a precipitate and is recovered by filtration.

For Reaction Step (L), a mole amount of a $C_1$–$C_4$ alkyl ester of 2-methyl-3-($C_1$–$C_4$ alkoxy, $C_1$–$C_4$ haloalkoxy 2-methoxyethoxy or 2-ethoxyethoxy)-4-($C_1$–$C_4$ alkylthio)benzoic acid is hydrolyzed with a base such as sodium hydroxide to the corresponding 2-methyl-3-($C_1$–$C_4$ alkoxy or $C_1$–$C_4$ haloalkoxy)-4-($C_1$–$C_4$ alkylthio)benzoic acid. The hydrolysis is run in a solvent such as an 89 percent methanol-water mixture. The reaction can be run at 25° to 100° C. with stirring the desired reaction product is recovered by conventional techniques.

For Reaction Step (M), a mole amount of 2-methyl-3-hydroxy benzoic acid is reacted with at least 2 mole of nitric acid in a solvent such as glacial acetic acid. The reaction can be run at room temperature and the reaction product recovered by conventional techniques.

For Reaction Step (N), 2-methyl-3-hydroxy-4-nitrobenzoic acid is needed with 2 mole of $C_1$–$C_4$ alkyl iodide or $C_1$–$C_4$ alkyl chloride and 2 mole of a base such as potassium carbonate in a solvent such as a mixture of acetone and DMF. The reaction can be run at reflux temperatures and the reaction product is recovered by conventional techniques.

The reaction product is the $C_1$–$C_4$ alkyl ester of 2-methyl-3-($C_1$–$C_4$ alkoxy)-4-nitrobenzoic acid. The $C_1$–$C_4$ alkyl groups will be identical. The reaction product is useful per se as an intermediate or can be used as a reactant in Reaction Step (H)-(L) described hereinafter.

The intermediate benzoic acids described herein can easily be converted to their respective acid chlorides and then to their acid cyanides, if desired, by the following two reactions. First, a mole of oxalyl chloride and a catalytic amount of dimethylformamide in a suitable solvent such as methylene chloride at a temperature of 20° to 40° C. for 1 to 4 hours is heated with a mole of the intermediate benzoic acid. The corresponding benzoic acid cyanide can easily be prepared from the benzoic acid chloride by reaction with cuprous cyanide at a temperature of 50° to 220° C. for 1 to 2 hours. These acid chlorides can be reacted with the above-described 1,3-cyclohexanedione to prepare the above-described herbicidal 2,3,4-trisubstituted benzoyl-1,3-cyclohexanediones according to the following two-step reaction.

The trisubstituted benzoic acid chloride intermediates are useful in the preparation of the previously described herbicidal 2-(2'3'4'-trisubstituted benzoyl)-1,-3-cyclohexanediones.

The following series of examples teach the synthesis of representative intermediate compounds of this invention. The structures of all compounds of the examples and tables were verified by nuclear magnetic resonance (NMR), infrared spectroscopy (IR) and mass spectroscopy (MS).

EXAMPLE I 3-hydroxy-2-methylbenzoic acid

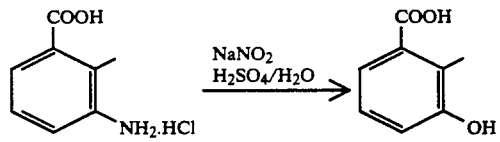

To a suspension of the anilinium hydrochloride salt (12.5 grams (g), 0.067 mol) in $H_2O$/ice/concentrated $H_2SO_4$ (60 milliliters (ml)/37 g/37 ml) was added a solution of $NaNO_2$ (4.76 g, 0.069 mol) in $H_2O$ (12 ml) slowly over 5 minutes. The reaction temperature was maintained at 5° C. with external cooling by an ice bath. The solid went into solution and the yellow solution was stirred for another 15 minutes. The solution was transferred to an addition funnel and added dropwise over 25 minutes to a heated solution of concentrated $H_2SO_4/H_2O$ (44 ml/34 ml). The reaction mixture was heated at reflux for another 5 minutes, cooled to room temperature, then immersed in an ice bath. The precipitate formed was collected by suction filtration and dissolved in ethylacetate (EtOAc). The mother liquor was extracted twice with EtOAc. The combined EtOAc layers were dried over magnesium sulfate ($MgSO_4$), filtered, and concentrated to a yellow solid (10.0 g, 0.065 mol, 97 percent yield). The structure of the compound was verified by nuclear magnetic resonance (NMR), infrared spectroscopy (IR) and mass spectroscopy (MS).

EXAMPLE II

Ethyl 3-hydroxy-2-methylbenzoate

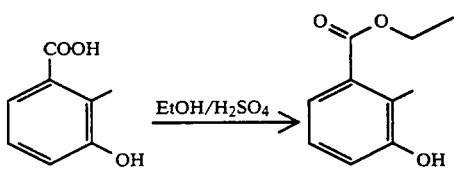

To a solution of the acid (8.0 g, 0.053 mol) in anhydrous ethanol (250 ml) was added the concentrated sulfuric acid (1.0 ml). The reaction mixture was allowed to heat at reflux for 20 hours and then cooled to room temperature. The ethanol was removed on the rotoevaporator and the residue was dissolved in EtOAc. The organic layer was washed sequentially with $H_2O$, aqueous saturated $NaHCO_3$ (2x), $H_2O$, dried ($MgSO_4$), filtered, and concentrated to a solid (5.6 g, 0.031 mol,

EXAMPLE III

Ethyl 4-bromo-3-hydroxy-2-methylbenzoate

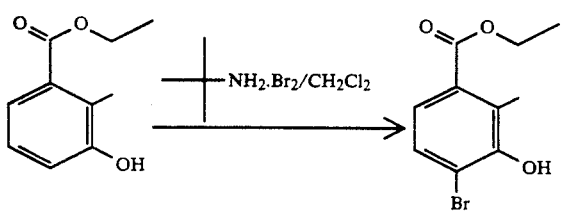

To a solution of the tert-butylamine (1.9 g, 0.026 mol) in CH$_2$Cl$_2$ (100 ml) at −78° C. was added a solution of bromine (4.08 g, 0.026 mol) in CH$_2$Cl$_2$ (30 ml) dropwise over 30 minutes. The mixture was stirred at −78° C. for another 30 minutes. A solution of the phenol (4.6 g, 0.026 mol) in CH$_2$Cl$_2$ (30 ml) was then added dropwise over 30 minutes. The reaction mixture was allowed to warm to room temperature and stir for 18 hours. Aqueous work-up followed by flash column chromatography purification (silica, 5.5:1; Hexanes:Et$_2$O) yielded the product as a yellow oil (2.8 g, 42%). The structure of the compound was verified by nuclear magnetic resonance (NMR), infrared spectroscopy (IR) and mass spectroscopy (MS).

EXAMPLE IV

Ethyl 4-bromo-3-ethoxy-2-methylbenzoate

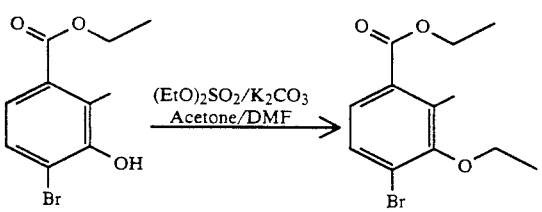

A mixture of the phenol (2.6 g, 0.01 mol), diethyl sulfate (1.7 g, 0.011 mol), and K$_2$CO$_3$ (1.52 g, 0.011 mol) in acetone/DMF (20 ml/20 ml) was heated at reflux for 50 minutes then allowed to cool to room temperature and stir over night. The reaction mixture was filtered and the solvent acetone was removed on the rotoevaporator. The residue was poured onto ice/H$_2$O. The organic material was extracted into hexanes (2x). The combined hexanes layers were dried (MgSO$_4$), filtered, and concentrated to an oil (3.0 g, 0.01 mol, 100%). The structure of the compound was verified by nuclear magnetic resonance (NMR), infrared spectroscopy (IR) and mass spectroscopy (MS).

EXAMPLE V

Ethyl 3-ethoxy-2-methyl-4-methylthiobenzoate

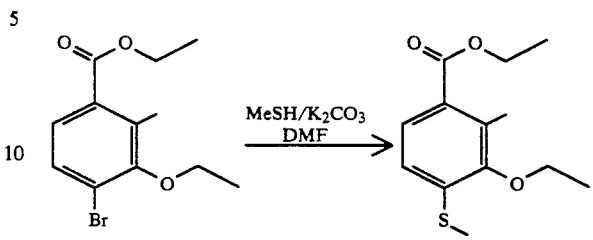

Methane thiol (1.5 g, 0.03 mol) was condensed into a stirred mixture of the bromo starting material (2.8 g, 0.01 mol), K$_2$CO$_3$ (2.07 g, 0.015 mol) in DMF (30 ml) at 0° C. The reaction vessel was rinsed with acetone (10 ml). The mixture was stirred at room temperature over night then heated at reflux for 6 hours. Gas chromatography analysis indicated 54% completion. The mixture was again cooled to 0° C. and more CH$_3$SH (2.5 g, 0.05 mol) was condensed in and more K$_2$CO$_3$ (4.6 g, 0.033 mol) was added. The mixture was again brought to reflux for 6 hours. After cooling to room temperature, the reaction mixture was poured into ice cold aqueous 1N HCl. The organic materials were extracted into Et$_2$O (2x). The combined organic layers were washed with 1N HCl, 5% K$_2$CO$_3$ (2x), dried (MgSO$_4$), filtered, and concentrated to an oil (2.25 g, 0.009 mol, 90%). The structure of the compound was verified by nuclear magnetic resonance (NMR), infrared spectroscopy (IR) and mass spectroscopy (MS).

EXAMPLE VI 3-ethoxy-2-methyl-4-methylthiobenzoic acid

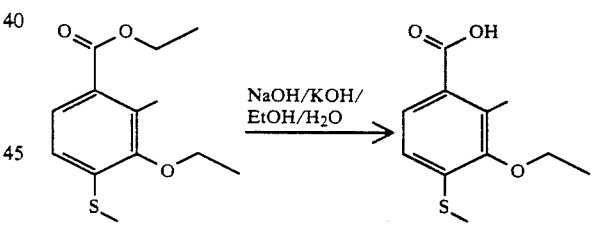

To a solution of the ester (2.2 g, 0.009 mol) in THF (20 mol) was added H$_2$O (20 ml) followed by solid NaOH (1.7 g, 0.043 mol). The mixture was stirred at room temperature for 2 hours then at reflux for another 2 hours. KOH (2.4 g, 0.043 mol) and ethanol (5 ml) were added and the mixture was heated at reflux for 20 hours. The mixture, upon cooling to room temperature, was poured into a separatory funnel (the flask was rinsed with Et$_2$O). The layers were separated and the organic layer was extracted with aqueous 5% K$_2$CO$_3$. The combined basic layers were acidified at low temperature with concentrated HCl and the desired acid was extracted into EtOAc. The EtOAc layer was dried (MgSO$_4$), filtered, and concentrated to an off white solid (2.2 g, 100%) m.p. 193°–196° C. The structure of the compound was verified by nuclear magnetic resonance (NMR), infrared spectroscopy (IR) and mass spectroscopy (MS).

EXAMPLE VII 3-ethoxy-2-methyl-4-methylsulfonylbenzoic acid

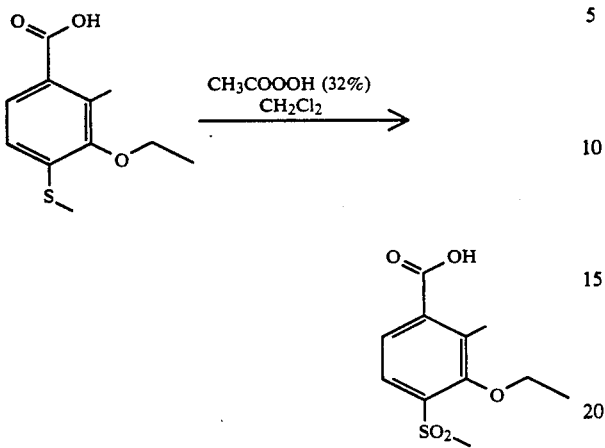

To a suspension of the acid (2.2 g, 0.01 mol) in CH$_2$Cl$_2$ (50 ml) at 0° C. was added the solution of 32% peracetic acid (4.6 ml, 0.022 tool) slowly. The solid went into solution and the mixture was allowed to warm to room temperature and stir for 3 days. More peracetic acid (1 ml) was added and the mixture was heated at reflux for 20 hours. The mixture was poured into a separatory funnel and the CH$_2$Cl$_2$ layer was washed once with H$_2$O. The H$_2$O layer was backextracted with CH$_2$Cl$_1$. The combined organic layers were dried (MgSO$_4$), filtered, and concentrated to a white solid (2.3 g, 90%) m.p. 132°-136° C. The structure of the compound was verified by nuclear magnetic resonance (NMR), infrared spectroscopy (IR) and mass spectroscopy (MS).

EXAMPLE VIII

Ethyl 2-methyl-3-hydroxy-4-nitrobenzoate

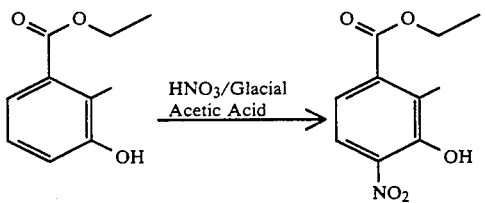

To a solution of the phenol (0.5 g, 0.0028 mol) in glacial acetic acid was added the ice (10 g) followed by concentrated nitric acid (specific gravity 1.42; 0.2 ml, 0.003 mol). The mixture was then stirred at room temperature for 45 minutes and another portion of nitric acid (0.2 ml, 0.003 mol) was added. Stirring was continued for one hour and excess ice was added to the reaction mixture. A yellow solid precipitated and was collected by suction filtration. Air-drying yielded the desired nitrated phenol (0.3 g, 48%). The structure of the compound was verified by nuclear magnetic resonance (NMR), infrared spectroscopy (IR) and mass spectroscopy (MS).

The process proceeds via the production of an enol ester intermediate as shown in reaction (1). The final product is obtained by rearrangement of the enol ester as shown in reaction (2). The two reactions may be conducted as separate steps by isolation and recovery of the enol ester using conventional techniques prior to conducting step (2), or by addition of a cyanide source to the reaction medium after the formation of the enol ester, or in one step by inclusion of the cyanide source at the start of reaction (1).

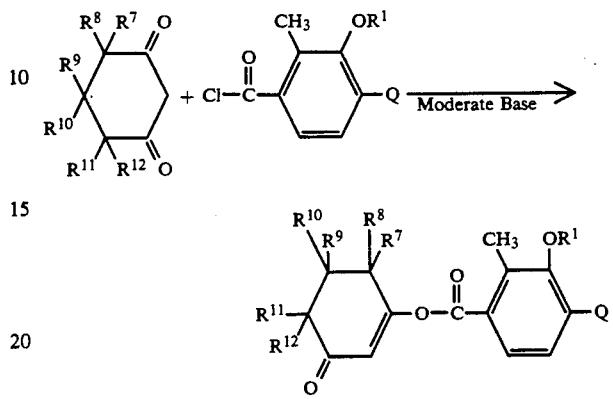

wherein n and $R^1$ $R^3$ and $R^7$ through $R^{12}$ are as defined above Q is halogen, nitro of $-S(O)_nR^2$ wherein $R^2$ is as defined above and the moderate base is such as tri-$C_1$-$C_6$ alkylamine, pyridine, alkali metal carbonate, or alkali metal phosphate.

Generally, in step (1) mole amounts of the dione and substituted benzoyl chloride are used, along with a slight mole excess of a moderate base. The two reactants are combined in an organic solvent such as acetonitrile, methylene chloride, toluene, ethyl acetate or dimethylformamide. The base and benzoyl reactant preferably are added to the reaction mixture with cooling. The mixture is stirred at 0° C.-50° C. until the reaction is substantially complete.

The reaction product is worked up by conventional techniques.

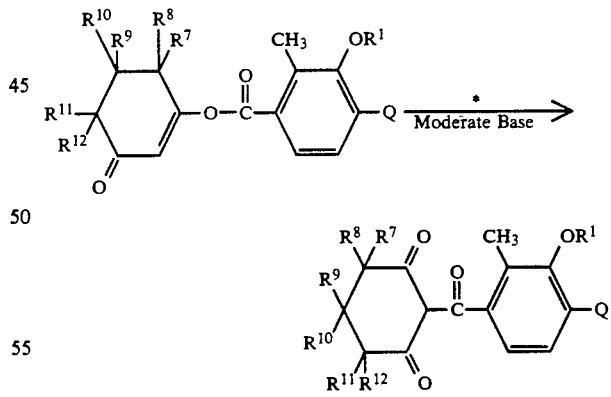

wherein $R^1$, $R^2$ and $R^7$ through $R^{12}$ and Q are as defined above

Generally, in step (2) a mole of the enol ester intermediate is reacted with 1 to 4 moles of the base, preferably about 2 moles of moderate base and from 0.01 mole to about 0.5 mole or higher, preferably around 0.1 mole of the cyanide source (e.g., potassium cyanide or acetone cyanohydrin). The mixture is stirred in a reaction pot until the rearrangement is substantially complete at a temperature below 80° C., preferably about 20° C. to about 40° C., and the desired product is recovered by conventional techniques.

The term "cyanide source" refers to a substance or substances which under the rearrangement conditions consists of or generates hydrogen cyanide and/or cyanide anion.

The process is conducted in the presence of a catalytic amount of a source of cyanide anion and/or hydrogen cyanide, together with a molar excess, with respect to the enol ester, of a moderate base.

Preferred cyanide sources are alkali metal cyanides such as sodium and potassium cyanide; cyanohydrins of methyl alkyl ketones having from 1-4 carbon atoms in the alkyl groups, such as acetone or methyl isobutyl ketone cyanohydrins; cyanohydrins of benzaldehyde or of $C_2$-$C_5$ aliphatic aldehydes such as acetaldehyde, propionaldehyde, etc., cyanohydrins; zinc cyanide; and hydrogen cyanide itself. Hydrogen cyanide is considered most advantageous as it produces relatively rapid reaction and is inexpensive. Among cyanohydrins the preferred cyanide source is acetone cyanohydrin.

The cyanide source is used in an amount up to about 50 mole percent based on the enol ester. It may be used in as little as about 1 mole percent to produce an acceptable rate of reaction at about 40° C. on a small scale. Larger scale reactions give more reproducible results with slightly higher catalyst levels of about 2 mole percent. Generally about 1–10 mole percent of the cyanide source is preferred.

The process is conducted with a molar excess, with respect to the enol ester, of a moderate base. By the term "moderate base" is meant a substance which acts as a base yet whose strength or activity as a base lies between that of strong bases such as hydroxides (which could cause hydrolysis of the enol ester) and that of weak bases such as bicarbonates (which would not function effectively). Moderate bases suitable for use in this embodiment include both organic bases such as tertiary amines and inorganic bases such as alkali metal carbonates and phosphates. Suitable tertiary amines include trialkylamines such as triethylamine, trialkanolamines such as triethanolamine, and pyridine. Suitable inorganic bases include potassium carbonate and trisodium phosphate.

The base is used in an amount of from about 1 to about 4 moles per mole of enol ester, preferably about 2 moles per mole.

When the cyanide source is an alkali metal cyanide, particularly potassium cyanide, a phase transfer catalyst may be included in the reaction. Particularly suitable phase transfer catalysts are the Crown ethers.

A number of different solvents may be usable in this process, depending on the nature of the acid chloride or the acylated product. A preferred solvent for this reaction is 1,2-dichloroethane. Other solvents which may be employed depending on the reactants or products include toluene, acetonitrile, methylene chloride, ethyl acetate, dimethylformamide, and methyl isobutyl ketone (MIBK).

In general, depending on the nature of the reactants and the cyanide source, the rearrangement may be conducted at temperatures up to about 50° C.

What is claimed is:
1. A compound having the structural formula

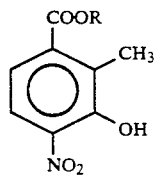

wherein R is $C_1$–$C_4$ alkyl.

2. The compound of claim 1 wherein R is ethyl.

* * * * *